United States Patent [19]

Mues et al.

[11] 4,229,445
[45] Oct. 21, 1980

[54] SYNERGISTIC ARTHROPODICIDAL COMPOSITIONS AND METHODS OF USE

[75] Inventors: Volker Mues, Wuppertal; Wolfgang Behrenz, Overath, both of Fed. Rep. of Germany

[73] Assignee: Bayer Aktiengesellschaft, Leverkusen, Fed. Rep. of Germany

[21] Appl. No.: 923,872

[22] Filed: Jul. 12, 1978

[30] Foreign Application Priority Data

Jul. 28, 1977 [DE] Fed. Rep. of Germany ....... 2734108

[51] Int. Cl.$^2$ .................. A01N 9/36; A01N 9/28; A01N 9/02; A01N 9/12
[52] U.S. Cl. .................................... 424/200; 424/202; 424/210; 424/211; 424/216; 424/212; 424/217; 424/220; 424/203; 424/218; 424/219; 424/222; 424/225; 424/274; 424/278; 424/282; 424/283; 424/300; 424/304; 424/305; 424/306; 424/341; 424/354; 260/340.5 R; 424/273 P; 424/275; 424/251; 424/214; 424/277
[58] Field of Search ............... 424/282, 200, 300, 305, 424/306, 225, 354; 260/340.5

[56] References Cited

U.S. PATENT DOCUMENTS

| | | | |
|---|---|---|---|
| 2,521,811 | 12/1950 | Wachs | 424/282 X |
| 3,310,463 | 3/1967 | Hopkins et al. | 424/282 |
| 3,338,783 | 8/1967 | Popjak | 424/282 X |
| 3,940,487 | 2/1976 | La Croix et al. | 424/282 |
| 3,962,415 | 8/1976 | Hennart et al. | 424/19 |

*Primary Examiner*—Leonard Schenkman
*Attorney, Agent, or Firm*—Sprung, Felfe, Horn, Lynch & Kramer

[57] ABSTRACT

A synergistic arthropodicidal composition comprising (a) a benzodioxole derivative of the formula

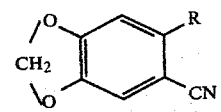

in which R represents alkyl, alkenyl, alkynyl, aryl or aralkyl, plus (b) at least one compound selected from (A) carbamates, (B) carboxylic acid esters, (C) phosphoric and phosphonic acid esters and (D) halogenoalkanes, and its use in combating arthropods.

6 Claims, No Drawings

SYNERGISTIC ARTHROPODICIDAL COMPOSITIONS AND METHODS OF USE

The present invention relates to new arthropodicidal, especially insecticidal and acaricidal, synergistic combinations of certain benzodioxoles, some of which are known, and certain other, known pesticidal active compounds.

It is already known that the following active compounds or groups of active compounds exhibit pesticidal, especially insecticidal and acaricidal, properties:

(A) Carbamates, for example 2-iso-propoxy-phenyl N-methyl-carbamate, 3,4,5-trimethyl-phenyl N-methyl-carbamate, 1-naphthyl N-methyl-carbamate, 2,3-dihydro-2,2-dimethyl-7-benzofuranyl N-methylcarbamate, 2-[1,3-dioxolan-2-yl-phenyl] N-methyl-carbamate and 2,2-dimethyl-1,3-benzodioxol-4-yl N-methyl-carbamate;

(B) carboxylic acid esters, for example 2,3,4,5-tetrahydrophthalimidomethyl chrysanthemate and (5-benzyl-3-furyl)-methyl 2,2-dimethyl-3-(2-methyl-propenyl)-cyclopropane-carboxylate;

(C) phosphoric acid esters, for example, O,O-dimethyl-O-(2,2-dichlorovinyl)-phosphoric acid ester; and (D) halogenoalkanes, for example 1,1,1-trichloro-2,2-bis-(4-methoxyphenyl)-ethane and 1,1,1-trichloro-2,2-bis-(4-chlorophenyl)-ethane.

Furthermore, synergistic mixtures of carbamates, for example 2-iso-propoxy-phenyl N-methylcarbamate, or of phosphoric acid esters, for example O,O-diethyl-O-[2-isopropyl-4-methyl-pyrimidin-6-yl]-thionophosphoric acid ester, or of natural or synthetic pyrethroids with piperonyl ethers, for example α-[2-(2-butoxyethoxy)-ethoxy]-4,5-methylenedioxy-2-propyl-toluene, are known (see Bull. Org. mond. Santé, Bull. Wld. Hlth. Org. 1966, 35, pages 691–708, Schrader, G., Die Entwicklung neuer insektizider Phosphorsäureester (The Development of New Insecticidal Phosphoric Acid Esters), 1963, page 158; and Perkov, W., Die Insektizide (The Insecticides), 1966, pages 516–524). However, the activity of these synergistic active compound combinations is not satisfactory. Hitherto, only α-[2-(2-butoxyethoxy)-ethoxy]-4,5-methylenedioxy-2-propyl-toluene (piperonyl butoxide) has attained some importance in practice.

The present invention now provides an arthropodicidal composition containing as active ingredients (1) a benzodioxole derivative of the general formula

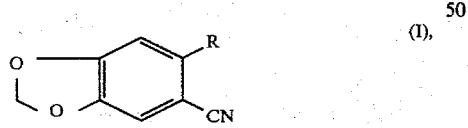

in which R represents alkyl, alkenyl, alkynyl, aryl or aralkyl, and (2) at least one compound selected from (A) carbamates, (B) carboxylic acid esters (which expression includes the natural and synthetic pyrethroids), (C) phosphoric and phosphonic acid esters and (D) halogenoalkanes, alone or in admixture with a solid or liquid or liquefied gaseous diluent or carrier.

Surprisingly, the insecticidal and/or acaricidal action of the active compound combinations according to the invention is substantially greater than the action of the individual components or the sum of the actions of the individual components. It is furthermore substantially greater than the action of the previously known active compound combination of 2-iso-propoxy-phenyl N-methyl-carbamate and piperonyl butoxide. In addition, the benzodioxole derivatives of the formula (I) show an excellent synergistic activity not only with one class of active compounds but with active compounds from a great variety of groups of chemical compounds. Accordingly, the synergistic mixtures according to the invention represent a valuable enrichment of the art.

The preferred benzodioxole derivatives of the formula (I) are those in which R represents straight-chain or branched alkyl with 1 to 8 (especially 1 to 5) carbon atoms, straight-chain or branched alkenyl with 2 to 8 (especially 2 to 5) carbon atoms, straight-chain or branched alkynyl with 2 to 8 (especially 2 to 5) carbon atoms, phenyl or benzyl.

Preferred carbamates (A) are those of the general formula

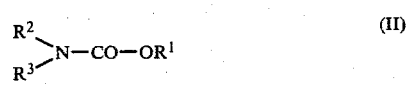

in which $R^1$ represents aryl, a heterocyclic ring or an oxime radical, $R^2$ represents hydrogen or alkyl with 1 to 4 carbon atoms and $R^3$ represents alkyl, alkylcarbonyl with 1 to 6 carbon atoms in the alkyl radical [which can optionally be substituted by hydroxyl or methylthio] or the —S—Z radical, in which Z represents an optionally halogen-substituted aliphatic radical with 1 to 4 carbon atoms (especially $CCl_3$ and $CF_3$), an aryl radical (especially phenyl) [which is optionally substituted by (preferably) nitrile, halogen (especially chlorine), methyl, trihalogenomethyl, trifluoromethylmercapto or nitro], methoxycarbonyl or the radical

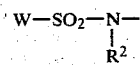

in which W represents $C_1$–$C_{20}$-alkyl, $C_1$–$C_5$-halogenoalkyl, $C_1$–$C_5$-alkylamino, $C_1$–$C_5$-dialkylamino or phenyl radical (which is optionally substituted (preferably) halogen, trihalogenomethyl, nitrile, methyl or nitro).

Particularly preferred carbamates (II) are those in which $R^1$ represents phenyl or naphthyl [either of which is optionally substituted by alkyl, alkenyl, alkoxy, alkylmercapto or alkylthioalkylene each with up to 5 carbon atoms, dialkylamino or dialkenylamino with up to 3 carbon atoms per alkyl or alkenyl part, halogen (especially chlorine), dioxolanyl or the radical —N=CH—N($C_{1-4}$-alkyl)$_2$].

Other particularly preferred carbamates (II) are those in which $R^1$ represents 2,3-dihydrobenzofuranyl, benzodioxole, benzothienyl, pyrimidinyl or pyrazolyl [each of which is optionally substituted by $C_{1-4}$-alkyl (especially methyl), or dialkylamino with 1 to 4 carbon atoms per alkyl part].

Further particularly preferred carbamates (II) are those in which $R^1$ represents an oxime radical of the general formula

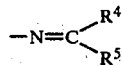 (IIa)

in which
R⁴ and R⁵, which may be identical or different, each represent alkyl, cycloalkyl, alkenyl, alkynyl, alkoxy, alkylmercapto, alkoxycarbonyl, carbonylamide or alkylmercaptoalkyl each with up to 5 carbon atoms, nitrile, aryl (especially phenyl), an optionally substituted heterocyclic radical with up to 9 carbon atoms or C₁-C₅-alkyl which is substituted by a heterocyclic radical, or
R⁴ and R⁵ conjointly represent a dioxolanyl or dithiolanyl radical which is optionally substituted by C₁₋₄-alkyl.

Preferred carboxylic acid esters (B) are those of the general formula

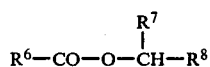 (III)

in which
R⁶ represents alkyl, aralkyl, aryl or cycloalkyl, each of which can optionally be substituted,
R⁷ represents hydrogen, alkyl, halogenoalkyl, alkenyl, alkynyl or nitrile and
R⁸ represents aryl or a heterocyclic ring, or R⁷ and R⁸ together form an optionally substituted cyclopentenone ring.

Particularly preferred carboxylic acid esters (III) are those in which
R⁶ represents alkyl with 1 to 6 carbon atoms [which is optionally substituted by optionally halogen-substituted phenyl], cyclopropyl [which is optionally substituted by alkyl, alkenyl, halogenoalkyl or halogenoalkenyl, each with up to 6 carbon atoms] or phenyl [which is optionally substituted by halogen], and/or
R⁷ represents hydrogen, alkyl with 1 to 6 carbon atoms, halogenoalkyl with 1 to 4 carbon atoms and up to 3 halogen atoms, nitrile or ethynyl, and/or
R⁸ represents phenyl [which is optionally substituted by C₁₋₄-alkyl, halogen (especially fluorine or chlorine), optionally halogen-substituted or methyl-substituted phenoxy or optionally substituted benzyl], furanyl, tetrahydrophthalimido or benzodioxole [any of which is optionally substituted by halogen (especially chlorine), alkyl or alkenyl with up to 4 carbon atoms or benzyl] or cyclopentenone [which is optionally substituted by C₁₋₄-alkyl, furfuryl or C₂₋₅-alkenyl].

Furthermore, the naturally occurring pyrethroids are particularly preferred.

Preferred phosphoric and phosphonic acid esters (C) are those of the general formula

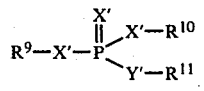 (IV)

in which
each X′, independently of any other, represents O or S,

Y′ represents O, S, —NH— or a direct bond between the central P atom and R¹¹,
R⁹ and R¹⁰, which may be identical or different, each represent optionally substituted alkyl or aryl, and
R¹¹ represents optionally substituted alkyl, aryl, heteroaryl, aralkyl, alkenyl or dioxanyl, an oxime radical or a radical identical to that to which it is bonded.

Particularly preferred phosphoric acid esters (IV) are those in which
R⁹ and R¹⁰, which may be identical or different, each represent C₁₋₄-alkyl or phenyl, and
R¹¹ represents alkyl with 1 to 4 carbon atoms [which is optionally substituted by halogen, hydroxyl, nitrile, optionally halogen-substituted phenyl, amidocarbonyl, C₁-C₁₀-alkylsulphonyl, C₁-C₁₀-alkylsulfoxy, C₁-C₁₀-alkylcarbonyl, C₁-C₁₀-alkoxy, C₁-C₁₀-alkylmercapto or C₁-C₁₀ alkoxycarbonyl], alkenyl with up to 4 carbon atoms [which is optionally substituted by halogen, optionally halogen-substituted phenyl or alkoxycarbonyl] or an oxime radical of the general formula

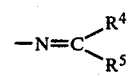 (IIa)

in which
R⁴ and R⁵ have the above-mentioned meanings (especially cyano or phenyl), or
R¹¹ represents dioxanyl which is substituted by a radical identical to that to which R¹¹ is bonded, or
R¹¹ represents a radical identical to that to which it is bonded or
R¹¹ represents phenyl [which is optionally substituted by methyl, nitro, nitrile, halogen or methylthio], or
R¹¹ represents an optionally C₁₋₄-alkyl-substituted or halogen-substituted hetero-aromatic structure (such as pyridine, quinoline, quinoxaline, pyrimidine, diazinone or benzo-1,2,4-triazine).

Preferred halogenoalkanes (D) are those of the general formula

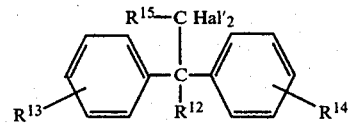 (V)

in which
Hal′ represents chlorine or bromine,
R¹² represents hydrogen or hydroxyl,
R¹³ and R¹⁴, which may be identical or different, each represent halogen, alkyl or alkoxy and
R¹⁵ represents hydrogen or halogen.

Particularly preferred halogenoalkanes (V) are those in which
R¹² denotes hydrogen or hydroxyl,
R¹³ and R¹⁴ are identical and represent halogen or alkyl or alkoxy with 1 to 4 carbon atoms and
R¹⁵ denotes halogen.

The following may be mentioned as examples of the benzodioxole derivatives of the formula (I) which can be used according to the invention: 6-methyl-, 6-ethyl-, 6-n-propyl-, 6-iso-propyl-, 6-n-butyl-, 6-iso-butyl-, 6- sec.-butyl-, 6-tert.-butyl-, 6-n-pentyl-, 6-iso-pentyl-, 6-tert.-pentyl-, 6-vinyl-, 6-allyl-, 6-propenyl-, 6-methallyl-, 6-crotonyl-, 6-but-1'-enyl-, 6-but-3'-enyl-, 6-ethynyl-, 6-prop-1'-ynyl-, 6-propargyl-, 6-phenyl- and 6-benzyl-3,4-methylenedioxy-benzonitrile.

Some of these compounds are new but can be prepared in accordance with processes known from the literature (see, for example, Pailer and Schleppnik, Monatshefte für Chemie 96, 1554–1562; ibidem, 98, 1603–1612).

The following equation illustrates the course of the reaction:

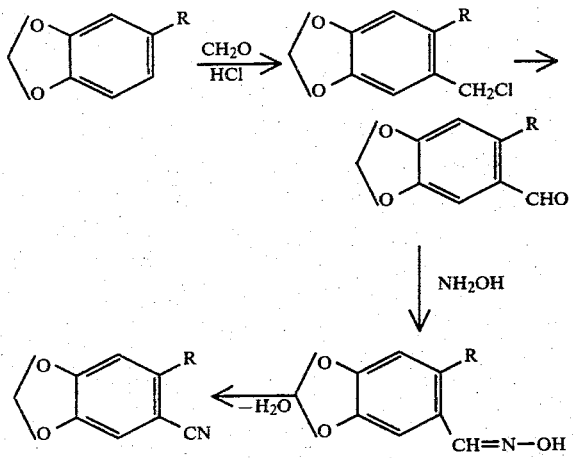

Where R represents n-propyl, the synthesis takes place via the following stages: safrol is hydrogenated to dihydrosafrol and is chloromethylated to give 6-chloromethyl-dihydrosafrol; a reaction with urotropine by Sommelet's method gives 6-n-propyl-piperonal. The aldoxime thereof is dehydrated with acetic anhydride to give 3,4-methylenedioxy-6-n-propylbenzonitrile.

The individual stages of the stated methods of synthesis are known or are carried out in accordance with methods which are in themselves known. For example, the preparation of the 6-chloromethyl compounds which in each case serve as intermediates can be carried out in accordance with the processes described in U.S. Pat. Nos. 2,485,600 and 2,485,680.

The carbamates (group A) of the formula (II), which may be used as components of the mixtures, include: 2-methylphenyl, 2-ethylphenyl, 2-n-propylphenyl, 2-methoxyphenyl, 2-ethoxyphenyl, 2-iso-propoxyphenyl, 4-methylphenyl, 4-ethylphenyl, 4-n-propylphenyl, 4-methoxyphenyl, 4-ethoxyphenyl, 4-n-propoxyphenyl, 3,4,5-trimethylphenyl, 1-naphthyl, 2,3-dihydro-2,2-dimethyl-7-benzofuranyl, 2-[1,3-dioxolan-2-yl-phenyl] and 2,2-dimethyl-1,3-benzodioxol-4-yl N-methyl-carbamate and the corresponding N-methyl-N-acetyl-, N-methyl-N-trifluoromethylthio-, N-methyl-N-dichloromonofluoromethylthio- and N-methyl-N-dimethylaminothio-carbamates.

These compounds, their preparation and their use are known (see, for example, U.S. Pat. Nos. 3,009,855, 2,903,478 and 3,111,539).

The carboxylic acid esters (group B) of the formula (III) which may be used as components of the mixtures include: 1-(3,4-dichlorophenyl)-2,2,2-trichloroethyl acetate, 2,3,4,5-tetrahydrophthalimidomethyl chrysanthemate and (5-benzyl-3-furyl)-methyl 2,2-dimethyl-3-(2-methylpropenyl)-cyclopropanecarboxylate. The compounds listed are known and in many cases are generally known commercial products [see R. Wegler "Chemie der Pflanzenschutz- und Schädlingsbekämpfungsmittel" ("Chemistry of Plant Protection Agents and Pesticides"), Volume 1, pages 87–118, Heidelberg (1970)].

The phosphoric and phosphonic acid esters (group C) of the formula (IV) which may used as components of the mixtures include: O,O-dimethyl- and O,O-diethyl-O-(2,2-dichloro- and 2,2-dibromovinyl)-phosphoric acid ester, O,O-diethyl-O-(4-nitro-phenyl)-thionophosphoric acid ester, O,O-dimethyl-O-(3-methyl-4-methylthio)-thionophosphoric acid ester, O,O-dimethyl-O-(3-methyl-4-nitro)-thionophosphoric acid ester, O-ethyl-S-n-propyl-O-(2,4-dichlorophenyl)-thionophosphoric acid ester, O-ethyl-S-n-propyl-O-(4-methylthiophenyl)-thionophosphoric acid ester, O,O-dimethyl-S-[4-oxo-1,2,3-benzotriazin-3-yl-methyl]-thionothiolphosphoric acid ester, O-methyl-O-[2-iso-propyl-6-methoxy-pyrimidin-4-yl]-thionomethanephosphonic acid ester, O,O-diethyl-O-[2-iso-propyl-6-methyl-pyrimidin-4-yl]-thionophosphoric acid ester, O,O-diethyl-O-[3-chloro-4-methyl-coumarin-7-yl]-thionophosphoric acid ester, O,O-dimethyl-2,2,2-trichloro-1-hydroxy-ethane-phosphonic acid ester and O,O-dimethyl-S-(methylcarbamoylmethyl)-thionophosphoric acid ester.

The compounds of the formula (IV) are known and are readily available in accordance with processes known from the literature (see, for example, U.S. Pat. No. 2,956,073, German Auslegeschrift (German Published Specification) No. 1,167,324 and Belgian Patent Specification No. 633,478).

The halogenoalkanes (group D) of the formula (V) which may be used as components of the mixtures include: 1,1,1-trichloro-2,2-bis-(4-chloro- and 4-methoxyphenyl)-ethane, 1,1,1-trichloro-2-hydroxy-2,2-bis-(4-chlorophenyl)-ethane and 1,1-dichloro-2,2-bis-(4-ethylphenyl)-ethane. These compounds, their preparation and their use are known (see, for example, U.S. Pat. Nos. 2,420,928, 2,464,600, 2,883,428 and 2,917,553).

The weight ratios of the groups of active compounds can vary within relatively wide ranges. In general, the weight ratio of benzodioxole derivative (1) to the other active compounds (2) is about 0.1:10 to 10:0.1. However, a weight ratio of about 0.5:1.0 to 3.0:1.0 has proved particularly suitable.

The active-compound combinations according to the invention not only result in a rapid knock-down action but also cause the persistent destruction of all or individual stages of development of animal pests, especially insects. The pests include those which occur in agriculture, forestry, the protection of stored products and the protection of materials, as well as in the field of hygiene. These include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera* spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae,*

*Blattella germanica, Acheta domesticus, Gryllotalpa* spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix*, Pemphigus spp., *Pediculus humanus corporis*, Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Laphygma exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example Scorpio maurus and *Latrodectus mactans;* from the order of the Acarina, for example *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp..

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The present invention also provides a method of combating arthropods, especially insects or acarids, which comprises applying to the arthropods, or to a habitat thereof, a composition according to the present invention.

The present invention also provides crops protected from damage by arthropods by being grown in areas in which immediately prior to and/or during the time of the growing a composition according to the present invention was applied.

The preparation of the synergistic agents (I) is shown in the following illustrative example:

EXAMPLE 1

(a) 6-Chloromethyl-dihydrosafrol 164.2 g (1.0 mol) of dihydrosafrol were stirred with 150 g of 40% strength formaldehyde solution and 500 g of concentrated hydrochloric acid for 36 hours at 20–30° C. The reaction mixture was then diluted with water and extracted with toluene, and the organic phase was washed with a sodium bicarbonate solution. After drying over sodium sulphate, the solution was concentrated and the residue was distilled. 173.5 g (82% of theory) of 6-chloromethyldihydrosafrol of boiling point 124° C./3 mm Hg were obtained.

(b) 6-n-Propyl-3,4-methylenedioxy-benzaldehyde 154 g (1.1 mol) of urotropine were added to a solution of 212.7 g (1.0 mol) of 6-chloromethyl-dihydrosafrol in 1,000 ml of methylene chloride, and the reaction mixture was heated under reflux, while stirring, for 4 hours. It was then cooled and the crystalline residue which had precipitated was filtered off and dried in air. This material was then stirred for 4 hours in 1,000 ml of 50% strength acetic acid under reflux, after which the mixture was cooled to 60° C., brought to pH 2 with concentrated hydrochloric acid and stirred under reflux for a further 10 minutes. Thereafter the reaction mixture was cooled, diluted with water and extracted with methylene chloride. The organic phase was washed until neutral, dried and concentrated and finally the residue was distilled. 137 g (71% of theory) of 6-n-propyl-3,4-methylenedioxy-benzaldehyde of boiling point 115° C./0.01 mm Hg were obtained.

(c) 6-n-Propyl-3,4-methylenedioxy-benzaldoxime 21.3 g (0.533 mol) of sodium hydroxide in 27 ml of water were added to a suspension of 37.1 g (0.533 mol) of hydroxylamine hydrochloride in 500 ml of ethanol and a solution of 77.0 g (0.4 mol) of 6-n-propyl-3,4-methylenedioxybenzaldehyde in 150 ml of ethanol was then added. After stirring for four hours under reflux, the reaction mixture was cooled, the solvent was stripped off and the residue was treated with water. The mixture was filtered and the residue was triturated with a mixture of petroleum ether and ether (6:1), again filtered off and dried in air. 72 g (87% of theory) of crystals of melting point 83° C. were obtained.

(d) 6-n-Propyl-3,4-methylenedioxy-gnmitrile

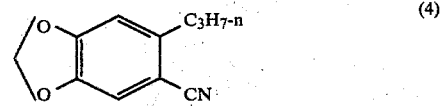

62.2 g (0.3 mol) of 6-n-propyl-3,4-methylenedioxybenzaldoxime were stirred with 400 ml of acetic anhydride for 3 hours under reflux, and the reaction solution was cooled and poured into water. It was left to stand for 2 hours and then extracted with toluene, and the organic phase was washed first with water, then with sodium bicarbonate solution and again with water until neutral. After drying over sodium sulphate, the organic phase was concentrated and distilled. 38 g (67% of theory) of boiling point 116° C./3 mm Hg were obtained.

The following could be prepared analogously:

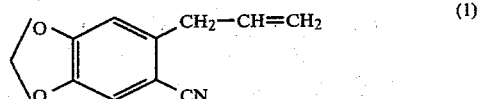

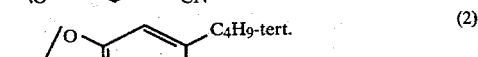

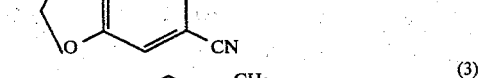

The arthropodicidal activity of the compositions of the present invention is illustrated by the following example wherein the synergistic benzodioxole derivatives of the general formula (I) are identified by the numbers (given in brackets) assigned to them in Example 1.

The known pesticidal compounds from the groups (A) to (D) are identified as follows:

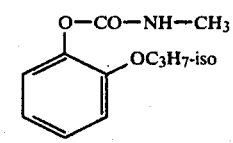 (A)

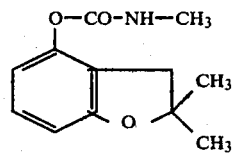 (B)

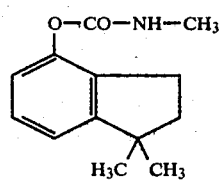 (C)

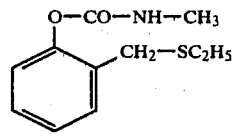 (D)

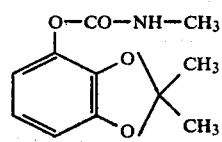 (E)

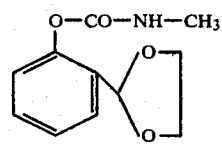 (F)

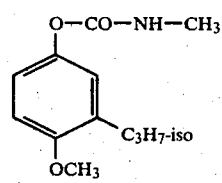 (G)

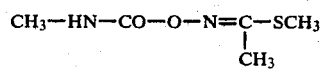 (H)

Pyrethrins as a 25% strength extract (I)

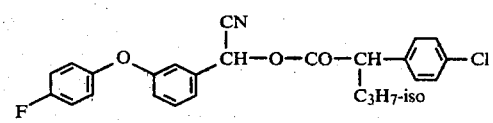 (K)

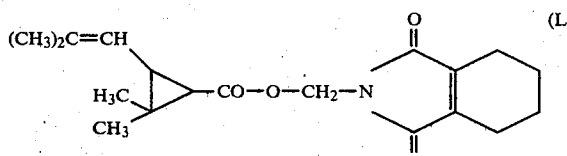 (L)

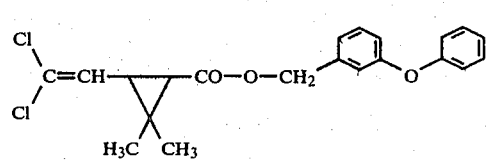 (M)

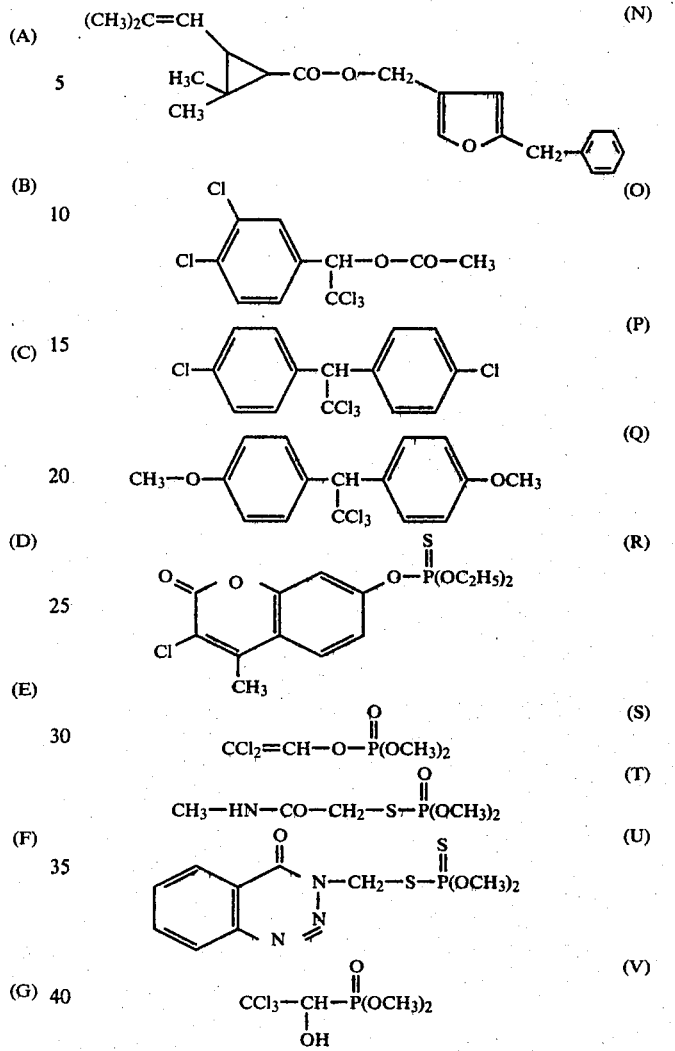

For comparison purposes, piperonyl butoxide

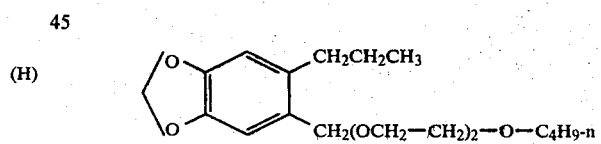

which is known in the prior art as a synergistic agent, was also employed.

EXAMPLE 2

$LT_{100}$ Test

Test insects Phosphoric acid ester-resistant *Musca domestica* (Weymanns strain)

Solvent: Acetone

Solutions were prepared from the active compounds, synergistic agents and mixtures of active compounds and synergistic agents, and 2.5 ml of each solution were pipetted onto a respective filterpaper of 9.5 cm diameter in a Petri dish. The filterpaper absorbed the solution. The Petri dish was left standing open until the solvent had completely evaporated. 25 test insects were then introduced into each Petri dish, and the dish was covered with a glass lid.

The condition of the test insects was checked continuously for up to 6 hours. The time required for a 100% knock down action was determined. If the $LT_{100}$ was not reached after 6 hours, the % of the test insects which had been knocked down was determined.

The concentrations of the active compounds, synergistic agents and mixtures, and their actions, can be seen from the table which follows.

Table

LT 100 Test with phosphoric acid ester-resistant *Musca domestica* (Weymanns strain)

| Active compounds Characterizing letter | Synergistic agents ( ) No. | Concentrations in % | LT 100 after minutes |
|---|---|---|---|
| A |  | 1.0 | 360' = 0% |
| B |  | 1.0 | 360' = 60% |
| C |  | 1.0 | 360' = 0% |
| D |  | 1.0 | 360' = 20% |
| E |  | 1.0 | 360' = 0% |
| F |  | 1.0 | 360' = 0% |
| G |  | 1.0 | 360' = 15% |
| H |  | 0.04 | 360' = 0% |
| I |  | 0.04 | 360' = 60% |
| K |  | 0.04 | 240' |
| L |  | 0.04 | 360' = 45% |
| M |  | 0.008 | 360' = 95% |
| N |  | 0.008 | 360' = 0% |
| O |  | 1.0 | 360' = 10% |
| P |  | 1.0 | 360' = 5% |
| Q |  | 1.0 | 360' = 20% |
| R |  | 1.0 | 360' = 0% |
| S |  | 0.008 | 360' = 90% |
| T |  | 0.04 | 360' = 25% |
| U |  | 1.0 | 360' = 65% |
| V |  | 1.0 | 360' = 45% |
|  | Piperonyl butoxide | 1.0 | 360' = 0% |
|  | (1) | 1.0 | 360' = 70% |
|  | (2) | 1.0 | 360' = 0% |
|  | (3) | 1.0 | 360' = 60% |
|  | (4) | 1.0 | 360' = 60% |
| A + | Piperonylbutoxide | 0.2 + 0.2 | 360' = 85% |
| A + | 1 | 0.008 + 0.008 | 240' |
| A + | 2 | 0.008 + 0.008 | 180' |
| A + | 3 | 0.008 + 0.008 | 150' |
| B + | Piperonylbutoxide | 0.2 + 0.2 | 360' = 95% |
| B + | 1 | 0.008 + 0.008 | 180' |
| B + | 2 | 0.008 + 0.008 | 210' |
| B + | 3 | 0.04 + 0.04 | 90' |
| C + | Piperonylbutoxide | 1.0 + 1.0 | 360' = 80% |
| C + | 1 | 0.2 + 0.2 | 360' |
| C + | 2 | 0.04 + 0.04 | 360' |
| C + | 3 | 0.04 + 0.04 | 360' |
| D + | Piperonylbutoxide | 0.2 + 0.2 | 360' = 0% |
| D + | 1 | 0.04 + 0.04 | 360' |
| D + | 2 | 0.04 + 0.04 | 360' = 85% |
| D + | 3 | 0.04 + 0.04 | 360' |
| E + | Piperonylbutoxide | 0.2 + 0.2 | 360' = 75% |
| E + | 1 | 0.008 + 0.008 | 240' |
| E + | 2 | 0.008 + 0.008 | 210' |
| E + | 3 | 0.008 + 0.008 | 180' |
| F + | Piperonylbutoxide | 1.0 + 1.0 | 360' = 90% |
| F + | 1 | 0.2 + 0.2 | 150' |
| F + | 2 | 0.2 + 0.2 | 180' |
| F + | 3 | 0.2 + 0.2 | 180' |
| G + | Piperonylbutoxide | 1.0 + 1.0 | 360' = 90% |
| G + | 1 | 0.04 + 0.04 | 120' |
| G + | 2 | 0.04 + 0.04 | 150' |
| H + | Piperonylbutoxide | 1.0 + 1.0 | 90' |
| H + | 1 | 1.0 + 1.0 | 60' |
| H + | 2 | 1.0 + 1.0 | 60' |
| J + | Piperonylbutoxide | 0.04 + 0.04 | 90' |
| J + | 1 | 0.04 + 0.04 | 75' |
| J + | 2 | 0.04 + 0.04 | 45' |
| K + | Piperonylbutoxide | 1.0 + 1.0 | 60' |
| K + | 1 | 1.0 + 1.0 | 30' |
| K + | 2 | 0.2 + 0.2 | 60' |
| L + | Piperonylbutoxide | 0.04 + 0.04 | 360' |
| L + | 1 | 0.04 + 0.04 | 120' |
| L + | 2 | 0.04 + 0.04 | 75' |
| M + | 1 | 0.008 + 0.008 | 90' |
| M + | 2 | 0.008 + 0.008 | 105' |
| N + | Piperonylbutoxide | 0.04 + 0.04 | 90' |
| N + | 1 | 0.04 + 0.04 | 45' |
| N + | 2 | 0.04 + 0.04 | 45' |
| O + | Piperonylbutoxide | 0.04 + 0.04 | 360' = 15% |
| O + | 1 | 0.04 + 0.04 | 360' |
| O + | 2 | 0.04 + 0.04 | 360' = 70% |
| P + | Piperonylbutoxide | 1.0 + 1.0 | 360' = 20% |
| P + | 1 | 0.2 + 0.2 | 210' |
| Q + | Piperonylbutoxide | 1.0 + 1.0 | 360' = 85% |
| Q + | 1 | 1.0 + 1.0 | 90' |
| Q + | 2 | 1.0 + 1.0 | 210' |
| Q + | 3 | 1.0 + 1.0 | 180' |
| R + | Piperonylbutoxide | 1.0 + 1.0 | 360' = 5% |
| R + | 1 | 1.0 + 1.0 | 360' = 95% |
| R + | 3 | 1.0 + 1.0 | 360' |
| S + | Piperonylbutoxide | 0.2 + 0.2 | 75' |
| S + | 1 | 0.2 + 0.2 | 45' |
| S + | 2 | 0.2 + 0.2 | 30' |
| S + | 3 | 0.2 + 0.2 | 30' |
| T + | Piperonylbutoxide | 0.04 + 0.04 | 360' = 60% |
| T + | 1 | 0.04 + 0.04 | 150' |
| T + | 2 | 0.04 + 0.04 | 120' |
| T + | 3 | 0.04 + 0.04 | 150' |
| U + | Piperonylbutoxide | 1.0 + 1.0 | 210' |
| U + | 1 | 1.0 + 1.0 | 60' |
| U + | 3 | 1.0 + 1.0 | 75' |
| V + | Piperonylbutoxide | 1.0 + 1.0 | 360' = 90% |
| V + | 1 | 1.0 + 1.0 | 240' |
| V + | 3 | 1.0 + 1.0 | 240' |

It will be appreciated that the instant specification and examples are set forth by way of illustration and not limitation, and that various modifications and changes may be made without departing from the spirit and scope of the present invention.

What we claim is:

1. A synergistic arthropodicidal composition comprising an arthropodicidally effective amount of (a) at least one compound selected from the group consisting of (A) carbamates, (B) carboxylic acid esters, (C) phosphoric and phosphonic acid esters and (D) halogenoalkanes, and an approximately equal weight of (b) a benzodioxole derivative of the formula

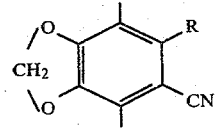

in which R represents alkyl with 1 to 6 carbon atoms, alkenyl with 2 to 8 carbon atoms, alkynyl with 2 to 8 carbon atoms, phenyl or benzyl.

2. A composition according to claim 1 in which
   (a) is at least one compound selected from (A) carbamates of the formula

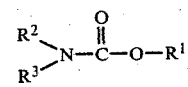

in which

R¹ represents aryl, a heterocyclic radical or an oxime radical,

R² represents hydrogen or alkyl with 1-4 carbon atoms and

R³ represents alkyl, alkylcarbonyl with 1-6 carbon atoms in the alkyl radical (which can be optionally substituted by hydroxyl or methylthio) or the radical —S—Z, wherein Z represents an optionally halogen-substituted aliphatic radical with 1 to 4 carbon atoms, an aryl radical (which is optionally substituted by nitrile, halogen, methyl, trihalogenomethyl, trifluoromethylmercapto or nitro), methoxycarbonyl or the radical $$W-SO_2-N-,$$
$$\phantom{W-SO_2-N}|$$
$$\phantom{W-SO_2-N-}R^2$$

wherein

W represents alkyl, halogenoalkyl, alkylamino or dialkylamino or an aryl radical (optionally substituted by halogen, trihalogenomethyl, nitrile, methyl or nitro), (B) carboxylic acid esters of the formula $$R^6-\overset{O}{\underset{\|}{C}}-O-\overset{R^7}{\underset{|}{CH}}-R^8$$

in which

R⁶ represents alkyl, aralkyl, aryl or cycloalkyl, each of which can be optionally substituted, R⁷ represents hydrogen, alkyl, halogenoalkyl, alkenyl, alkynyl or nitrile and R⁸ represents aryl or a heterocyclic radical, or R⁷ and R⁸ together form an optionally substituted cyclopentenone ring, and the naturally occurring pyrethroids, (C) phosphoric and phosphonic acid esters of the formula $$R^9-X'-\overset{X'}{\underset{\|}{P}}\overset{X'-R^{10}}{\underset{Y'-R^{11}}{\diagdown}}$$

in which each X', independently of any other, represents O or S,

Y' represents O, S, —NH— or a direct bond between the central P atom and the radical R¹¹, R⁹ and R¹⁰, which may be identical or different, each represent alkyl or aryl and R¹¹ represents optionally substituted alkyl, aryl, heteroaryl, aralkyl, alkenyl or dioxanyl, an oxime radical or a radical identical to that to which it is bonded and (D) halogenoalkanes of the formula

[structure with R¹⁵—CHal'₂, R¹³, R¹², R¹⁴]

in which

Hal' represents chlorine or bromine,

R¹² represents hydrogen or hydroxyl,

R¹³ and R¹⁴, which may be identical or different, each represent halogen, alkyl or alkoxy and R¹⁵ represents hydrogen or halogen.

3. A composition according to claim 2, in which (a) is at least one compound selected from (A) carbamates in which R¹ represents phenyl or naphthyl (either of which is optionally substituted by alkyl, alkenyl, alkoxy, alkylmercapto or alkylthioalkylene with up to 5 carbon atoms in each case, dialkylamino or dialkenylamino with up to 3 carbon atoms per alkyl or alkenyl part, halogen, dioxolanyl or the radical —N=CH—N(C₁₋₄-alkyl)₂), or R¹ represents 2,3-dihydrobenzofuranyl, benzodioxole, benzothienyl, pyrimidinyl or pyrazolyl (each of which is optionally substituted by C₁₋₄-alkyl or dialkylamino with 1-4 carbon atoms per alkyl part), or R¹ represents an oxime radical of the formula $$-N=C\overset{R^4}{\underset{R^5}{\diagdown}}$$

in which

R⁴ and R⁵ which may be identical or different, each represent alkkyl, cycloalkyl, alkenyl, alkynyl, alkoxy, alkylmercapto, alkoxycarbonyl, carbonylamide or alkylmercaptoalkyl with up to 5 carbon atoms in each case, nitrile, aryl, an optionally substituted heterocyclic radical or alkyl which is substituted by a heterocyclic radical, or R⁴ and R⁵ together form a dioxolanyl or dithiolanyl radical which is optionally substituted by C₁₋₄ alkyl, (B) carboxylic acid esters in which R⁶ represents alkyl with 1-6 carbon atoms (which is optionally substituted by optionally halogen-substituted phenyl), cyclopropyl (which is optionally substituted by alkyl, alkenyl, halogenoalkyl or halogenoalkenyl with up to 6 carbon atoms in each case) or phenyl (which is optionally substituted by halogen), R⁷ represents hydrogen, alkyl with 1-6 carbon atoms, halogenoalkyl with 1-4 carbon atoms and up to 3 halogen atoms, nitrile or ethynyl, and R⁸ represents phenyl (which is optionally substituted by C₁₋₄-alkyl, halogen, optionally halogen-substituted or methyl-substituted phenoxy or optionally substituted benzyl), furanyl, tetrahydrophthalimido or benzodioxole (any of which is optionally substituted by halogen, alkyl or alkenyl with up to 4 carbon atoms or benzyl) or cyclopentenone (which is optionally substituted by C₁₋₄-alkyl, furfuryl or C₂₋₅-alkenyl), (C) phosphoric and phosphonic acid esters in which $R^9$ and $R^{10}$, which may be identical or different, each represent $C_{1-4}$-alkyl or phenyl, and
$R^{11}$ represents alkyl with 1–4 carbon atoms (which is optionally substituted by halogen, hydroxyl, nitrile, optionally halogen-substituted phenyl, carbonylamide, sulphonylalkyl, sulphoxyalkyl, carbonylalkyl, alkoxy, alkylmercapto or alkoxycarbonyl), alkenyl with up to 4 carbon atoms (which is optionally substituted by halogen, optionally halogen-substituted phenyl or alkoxycarbonyl) or an oxime radical of the formula

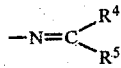

wherein
$R^4$ and $R^5$ have the meanings stated above, or $R^{11}$ represents dioxanyl which is substituted by a radical identical to that to which $R^{11}$ is bonded, or $R^{11}$ represents a radical identical to that to which it is bonded, or $R^{11}$ represents phenyl (which is optionally substituted by methyl, nitro, nitrile, halogen or methylthio), or $R^{11}$ represents a hetero-aromatic structure that is optionally substituted by $C_{1-4}$-alkyl or halogen, and
(D) halogenoalkanes in which
$R^{12}$ denotes hydrogen or hydroxyl,
$R^{13}$ and $R^{14}$ are identical and represent halogen, alkyl with 1 to 4 carbon atoms or alkoxy with 1 to 4 carbon atoms and
$R^{15}$ denotes halogen.

4. A composition according to claim 3, in which R is alkyl with 1 to 8 carbon atoms, alkenyl with 2 to 8 carbon atoms, alkynyl with 2 to 8 carbon atoms, phenyl or benzyl.

5. A method of combating arthropods which comprises applying to the arthropods, or to a habitat thereof, an arthropodicidally effective amount of a composition according to claim 1.

6. A method of combating arthropods which comprises applying to the arthropods, or to a habitat thereof, a composition according to claim 4.

* * * * *